US00PP20407P2

(12) United States Plant Patent
Perkins

(10) Patent No.: US PP20,407 P2
(45) Date of Patent: Oct. 13, 2009

(54) *ANGELONIA* PLANT NAMED 'CAR PURR09'

(50) Latin Name: *Angelonia angustifolia*
Varietal Denomination: Car Purr09

(75) Inventor: Ralph T. Perkins, Gilroy, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 12/220,632

(22) Filed: Jul. 25, 2008

(51) Int. Cl.
*A01H 5/00* (2006.01)

(52) U.S. Cl. ..... Plt./404

(58) Field of Classification Search ..... Plt./263, Plt./404
See application file for complete search history.

*Primary Examiner*—Susan B McCormick Ewoldt
(74) *Attorney, Agent, or Firm*—S. Matthew Edwards

(57) ABSTRACT

A new *Angelonia* plant named 'Car Purr09,' particularly distinguished by the purple flower color, upright and compact habit, dense foliage, strong stems, and good floriferousness.

1 Drawing Sheet

Latin name of the genus and species of the plant claimed: *Angelonia angustifolia.*

Varietal denomination: 'Car Purr09'.

BACKGROUND OF THE NEW PLANT

The present invention comprises a new *Angelonia*, botanically known as *Angelonia angustifolia,* and hereinafter referred to by the variety name 'Car Purr09.'

'Car Purr09' is a product of a planned breeding program. The new cultivar 'Car Purr09' has a purple flower color, upright and compact habit, with dense foliage, strong stems, and good floriferousness.

'Car Purr09' originated from a hybridization in a controlled breeding program in Gilroy, Calif. USA. The female parent was an unpatented hybrid seedling identified as '402-1' with deep lavender color. '402-1' has less branching, less floriferousness, and a taller plant habit compared to 'Car Purr09.'

The male parent of 'Car Purr09' was an unpatented hybrid seedling identified as '191-1' with purple and white color. '191-1' has less branching, less floriferousness, and a taller plant habit compared to 'Car Purr09.'

'Car Purr09' was selected as one flowering plant within the progeny of the stated cross in 2006, in a controlled environment in Gilroy, Calif. USA.

The first act of asexual reproduction of 'Car Purr09' was accomplished when vegetative cuttings were taken from the initial selection in March 2006. The pollination took place in August 2003 and the seed sowing in November 2005, all in Gilroy, Calif. USA in a controlled environment.

Horticultural examination of plants grown from cuttings of the plant initiated in March of 2006 in Gilroy, Calif. USA, and continuing thereafter, has demonstrated that the combination of characteristics as herein disclosed for 'Car Purr09' are firmly fixed and are retained through successive generations of asexual reproduction.

'Car Purr09' has not been observed under all possible environmental conditions. The phenotype may vary significantly with variations in environment such as temperature, light intensity and day length.

A Plant Breeder's Right for this cultivar was applied for in Canada on Dec. 24, 2007. 'Car Purr09' has not been made publicly available more than one year prior to the filing of this application.

DESCRIPTION OF THE DRAWING

The accompanying photographic drawing shows typical flower and foliage characteristics of 'Car Purr09' with colors being as true as possible with an illustration of this type. The photographic drawing shows a flowering potted plant of the new variety, and a close-up of the flowers.

The whole plant photograph was taken in the fall of 2007 and the close-up taken in the spring of 2008, both in Gilroy, Calif. USA. Both were grown in Gilroy, Calif. USA and were approximately 3–4 months old.

DETAILED BOTANICAL DESCRIPTION

The measurements were taken in Gilroy, Calif. USA in April 2008 on plants that were growing in one gallon pots in a greenhouse. Culture of these plants started January 2008 in a greenhouse. These plants were about 3 months old.

Color chart used: Royal Horticultural Society Colour Chart (R.H.S.) 2001.

BRIEF SUMMARY OF INVENTION

The following observations, measurements, and comparisons describe plants grown in Gilroy, Calif. The following traits have been repeatedly observed and are determined to be basic characteristics of the new variety. The combination of these characteristics distinguishes this *Angelonia* as a new and distinct variety.

TABLE 1

DIFFERENCES BETWEEN THE NEW VARIETY 'CAR PURR09' AND SIMILAR VARIETY

| | 'Car Purr09' | 'Balangdepi' (U.S. Plant Pat. No. 14,656) |
|---|---|---|
| Flower color | RHS 83A | RHS N87A |
| Plant branching | More | Less |
| Foliage size | Smaller | Larger |
| Plant height/size | Shorter, more compact | Taller, less compact |
| Flowering response | Earlier | Later |

Plant:
- *Form, growth and habit.*—Upright, compact habit with dense foliage.
- *Plant height.*—22–25 cm.
- *Plant height (inflorescence included).*—27–31 cm.
- *Plant width.*—20–24 cm.

Foliage:
- *Immature, leaf color, upper surface.*—Closest to RHS 146A.
- *Lower surface.*—Closest to RHS 146A but a little lighter.
- *Mature, leaf color, upper surface.*—Closest to RHS 147A.
- *Lower surface.*—Closest to RHS 146A but a little lighter.
- *Length.*—5.8–6.7 cm.
- *Width.*—1.1–1.4 cm.
- *Shape.*—Elliptical.
- *Base shape.*—Cuncate.
- *Apex shape.*—Acute.
- *Margin.*—Serrulate.
- *Texture.*—Few glandular hairs.
- *Color of veins, upper surface.*—RHS 144A.
- *Color of veins, lower surface.*—RHS 144A.

Stem:
- *Number of main stems per plant.*—4–5.
- *Number of leaves per stem (before it branches).*—12–14.
- *Color of stem.*—RHS 146A; some old basal stems have a little anthocyanin of RHS 166A but lighter.
- *Length of stem.*—23–26 cm.
- *Diameter.*—0.2–0.3 cm.
- *Length of internodes.*—1.5–2.5 cm.
- *Texture.*—Mostly glabrous but with a few glandular hairs.

Inflorescence:
- *Type.*—Terminal raceme; florets solitary in leaf axis.
- *Number of florets per raceme.*—20–26.
- *Raceme length.*—15–20 cm.
- *Color of pedicel.*—RHS N77A.
- *Length of pedicel.*—1.3–1.5 cm.
- *Diameter of pedicel.*—0.075 cm.
- *Texture.*—Mostly glabrous but with a few glandular hairs.

Corolla:
- *Form.*—Single, two-lipped (5-petaled, fused at base).
- *Length of floret.*—2.3–2.4 cm.
- *Width of floret.*—2.1–2.4 cm.
- *Color upper lip petals, upper surface.*—Closest to RHS 86A with slightly darker veining.
- *Color upper lip petals, lower surface.*—RHS 86B.
- *Size upper lip petal length.*—0.8–0.9 cm from corolla opening.
- *Size upper lip petal width.*—1.1–1.2 cm.
- *Color lower lip, lateral petals, upper surface.*—Closest to RHS 86A with slightly darker veining.
- *Color lower lip, lateral petals, lower surface.*—RHS 86B.
- *Size lower lip, lateral petals length.*—0.9–1.0 cm from corolla opening.
- *Size lower lip, lateral petals width.*—1.0–1.1 cm.
- *Color lower lip, mid-petal, upper surface.*—Closest to RHS 86A with slightly darker veining.
- *Color lower lip, mid-petal, lower surface.*—RHS 86B.
- *Size lower lip, mid-petal length.*—0.9–1.0 cm from corolla opening.
- *Size lower lip, mid-petal width.*—0.9–1.1 cm.
- *Petal shape.*—Obovate.
- *Apex shape.*—Obtuse.
- *Margin.*—Entire.
- *Petal texture.*—Papillose; few glandular hairs.
- *Corolla color, inside.*—RHS N155B ground color; RHS N92A spots.
- *Corolla color, outside.*—RHS 79A ground color; RHS N92A spots.
- *Duration of flowering.*—Continuous flowering throughout the summer.
- *Fragrance.*—None.
- *Lastingness of individual florets.*—About 7 days.

Bud (just before opening):
- *Color.*—RHS 83A but a little greyer.
- *Length.*—0.6–0.7 cm.
- *Width.*—0.5–0.6 cm.
- *Shape.*—Obovate.

Calyx:
- *Number of sepals.*—5, fused at base.
- *Color of sepals.*—RHS 146B to C.
- *Length of sepals.*—0.3–0.35 cm.
- *Width of sepals.*—0.15 cm.
- *Sepal shape.*—Ovate.
- *Apex shape.*—Acute.
- *Margins.*—Entire to almost slightly serrate.
- *Texture.*—Few glandular hairs.

Reproductive organs:
- *Pistil.*—1.
- *Length.*—0.3–0.35 cm.
- *Style color.*—Closest to RHS 75D.
- *Stigma color.*—RHS 76A.
- *Number of stamens.*—4, in pairs.
- *Length filaments.*—0.2–0.3 cm.
- *Color of filaments.*—RHS N155B.
- *Color of pollen.*—RHS N92D.
- *Pollen amount.*—Sparse.
- *Fertility/seed set.*—Not observed on this hybrid.

Disease/pest resistance: Disease resistance and/or susceptibility has not been observed on this hybrid.

What is claimed is:

1. A new and distinct variety of *Angelonia* plant named 'Car Purr09,' substantially as illustrated and described herein.

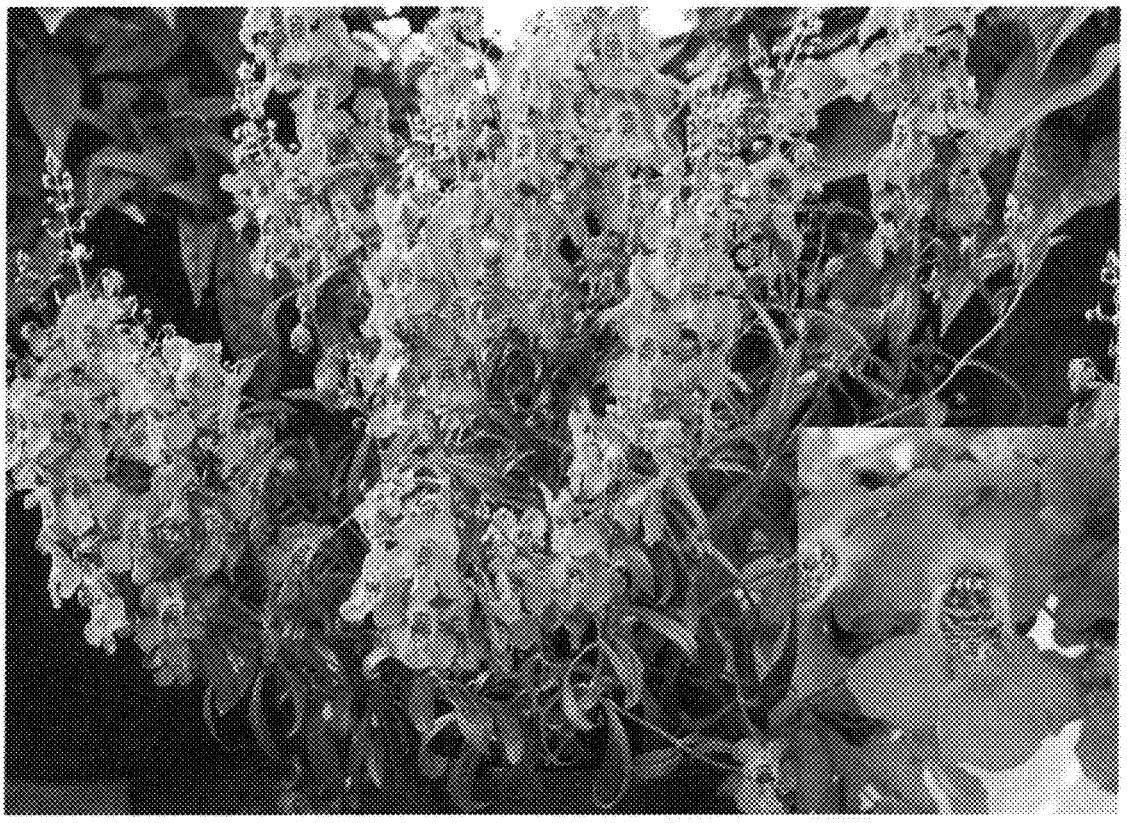

* * * * *